United States Patent
Hu et al.

(10) Patent No.: US 7,301,165 B2
(45) Date of Patent: Nov. 27, 2007

(54) METHODS AND APPARATUS FOR INSPECTING AN OBJECT

(75) Inventors: Qingying Hu, Clifton Park, NY (US); Kevin George Harding, Nishkayuna, NY (US); Joseph Benjamin Ross, Cincinnati, OH (US); Xiaoping Qian, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 93 days.

(21) Appl. No.: 11/256,904

(22) Filed: Oct. 24, 2005

(65) Prior Publication Data
US 2007/0090309 A1     Apr. 26, 2007

(51) Int. Cl.
*G01N 21/88* (2006.01)
*G01N 21/86* (2006.01)
*G01V 8/00* (2006.01)

(52) U.S. Cl. .............. 250/559.45; 250/559.4; 356/239.1; 356/237.2

(58) Field of Classification Search ............ 250/559.4, 250/559.42, 559.45; 356/237.1–237.6, 239.1–239.8
See application file for complete search history.

(56) References Cited

U.S. PATENT DOCUMENTS

| | | | |
|---|---|---|---|
| 4,585,947 A | 4/1986 | Liptay-Wagner et al. | |
| 4,686,374 A | 8/1987 | Liptay-Wagner et al. | |
| 5,307,151 A | 4/1994 | Hof et al. | |
| 5,495,337 A * | 2/1996 | Goshorn et al. | 356/601 |
| 6,028,671 A | 2/2000 | Svetkoff et al. | |
| 6,064,759 A | 5/2000 | Buckley et al. | |
| 6,639,685 B1 | 10/2003 | Gu et al. | |
| 6,678,057 B2 | 1/2004 | Harding et al. | |
| 7,019,826 B2 * | 3/2006 | Vook et al. | 356/237.1 |
| 7,098,435 B2 * | 8/2006 | Mueller et al. | 250/208.1 |
| 2002/0014577 A1 | 2/2002 | Ulrich et al. | |
| 2005/0111726 A1 | 5/2005 | Hackney et al. | |

OTHER PUBLICATIONS

Hu, Qingying, et al., Shiny Parts Measurement Using Color Separation, 8 page abstract, GE GRC, Schenectady, NY (Oct. 22, 2005).

* cited by examiner

*Primary Examiner*—Georgia Epps
*Assistant Examiner*—Patrick J. Lee
(74) *Attorney, Agent, or Firm*—Armstrong Teasdale LLP; William Scott Andes (57) ABSTRACT

A method for inspecting an object using a structured light measurement system that includes a light source for projecting light onto a surface of the object and an imaging sensor for receiving light reflected from the object. The method includes determining a position of at least one of the light source and the imaging sensor with respect to the object based on at least one of a three-dimensional model of the object and a three-dimensional model of the structured light measurement system.

20 Claims, 4 Drawing Sheets

METHODS AND APPARATUS FOR INSPECTING AN OBJECT

BACKGROUND OF THE INVENTION

This application relates generally to inspecting objects, and more specifically to methods and apparatus for inspecting objects using a light measurement system.

Objects are sometimes inspected, for example, to determine a size and/or shape of all or a portion of the object and/or to detect defects in the object. For example, some gas turbine engine components, such as turbine or compressor blades, are inspected to detect fatigue cracks that may be caused by vibratory, mechanical, and/or thermal stresses induced to the engine. Moreover, and for example, some gas turbine engine blades are inspected for deformations such as platform orientation, contour cross-section, bow and twist along a stacking axis, thickness, and/or chord length at given cross-sections. Over time, continued operation of the object with one or more defects may reduce performance of the object and/or lead to object failures, for example, as cracks propagate through the object. Accordingly, detecting defects of the object as early as possible may facilitate increasing the performance of the object and/or reducing object failures.

To facilitate inspecting objects, at least some objects are inspected using a light measurement system that projects a structured light pattern onto a surface of the object. The light measurement system images the structured light pattern reflected from the surface of the object and then analyzes the deformation of the reflected light pattern to calculate the surface features of the object. However, because many manufactured objects have a wide range of shapes and reflectivities, data obtained from some known light measurement systems may be less optimal than desired because of variables such as the angle of view of the light source, uneven reflections from the object, and/or noise caused by ambient light and/or multiple bounce reflections of the emitted light. Accordingly, such variables may result in reduced image quality and poor measurement results, possibly leading to an incorrect interpretation of surface features of the object.

Some known light measurement systems optimize the angle of view of the light source by taking a series of data sets and guessing at the best position of the light source based on the data sets. However, this may be difficult and/or time consuming. Moreover, at least some known light measurement systems include a physical mask that is formed, for example, from a sheet of paper or metal. The physical mask limits an area illuminated by the light source to facilitate reducing inter-reflections between the test fixture and the object. However, such physical masks are sometimes formed by electronically tracing an outline of the object as seen from the light source, which may be time consuming and/or difficult. Refinement of such masks is sometimes only done visually, which may further increase a time and/or difficulty of fabricating such a physical mask.

BRIEF DESCRIPTION OF THE INVENTION

In one aspect, a method is provided for inspecting an object using a structured light measurement system that includes a light source for projecting light onto a surface of the object and an imaging sensor for receiving light reflected from the object. The method includes determining a position of at least one of the light source and the imaging sensor with respect to the object based on at least one of a three-dimensional model of the object and a three-dimensional model of the structured light measurement system.

In another aspect, a method is provided for inspecting an object using a structured light measurement system that includes a light source for projecting light onto a surface of the object and an imaging sensor for receiving light reflected from the object. The method includes determining a position of at least one of the light source and the imaging sensor with respect to the object based on at least one of a three-dimensional model of the object and a three-dimensional model of the structured light measurement system, positioning at least one of the light source and the imaging sensor with respect to the object based on the determined position, emitting light from the light source, projecting light emitted from the light source onto a surface of the object, receiving light reflected from the object surface with the imaging sensor, and analyzing the light received by the imaging sensor to facilitate inspecting at least a portion of the object.

In another aspect, a structured light measurement system for inspecting an object includes a structured light source configured to project structured light onto a surface of the object, an imaging sensor configured to receive structured light reflected from the object surface, and a computer configured to determine a position of at least one of the structured light source and the imaging sensor with respect to the object based on at least one of a three-dimensional model of the object and a three-dimensional model of the structured light measurement system.

DETAILED DESCRIPTION OF THE INVENTION

Figure 1:
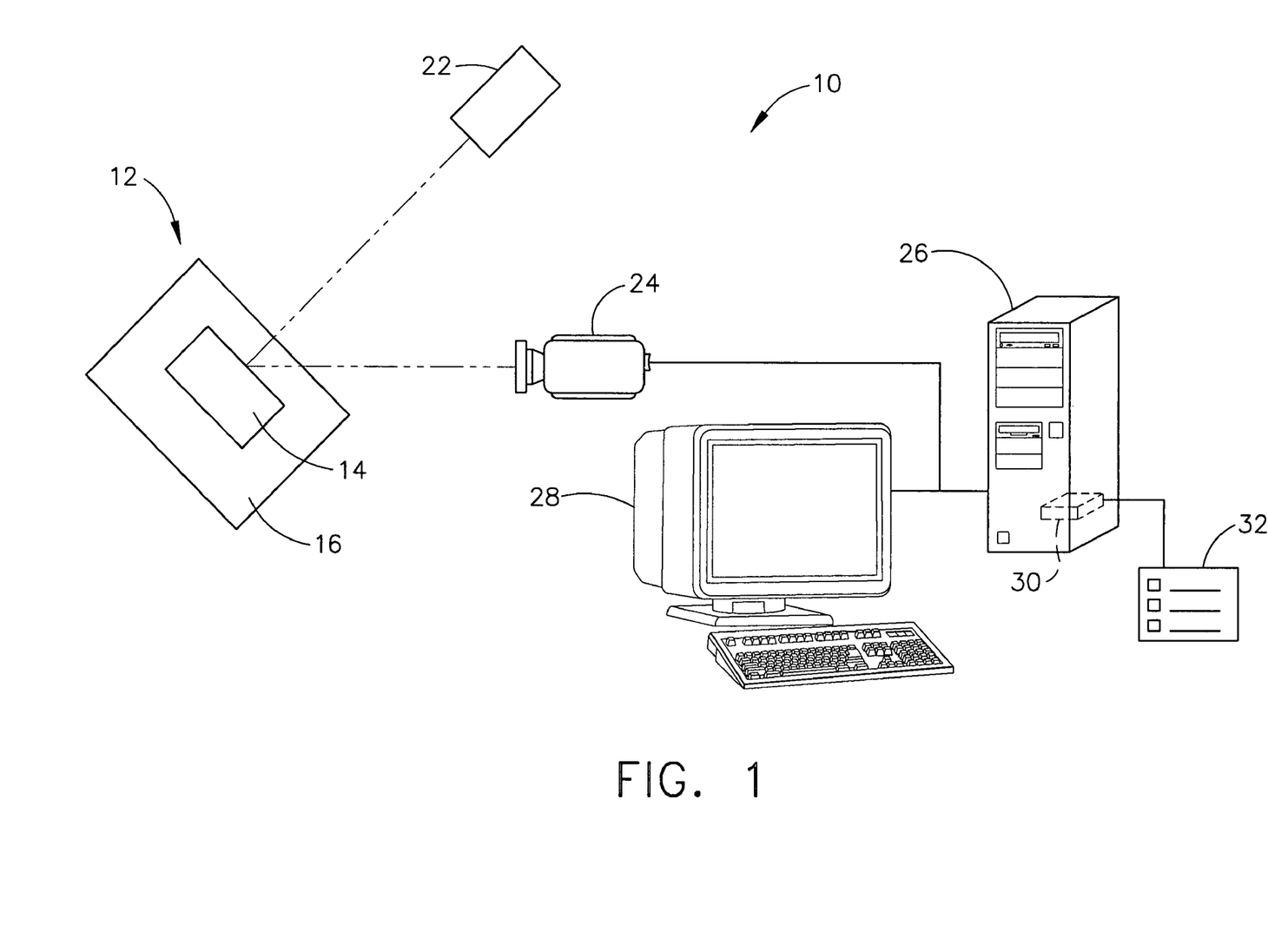
FIG. 1 is a block diagram of an exemplary embodiment of a structured light measurement system.

FIG. 1 is a block diagram of an exemplary embodiment of a structured light measurement system 10 that is used to measure a plurality of surface features of an object 12. For example, system 10 may be used to inspect and determine surfaces of object 12, wherein the surfaces may include features such as tilts, bends, twists, and/or warps when compared to a model representative of object 12.

In the exemplary embodiment, object 12 is a rotor blade, such as, but not limited to, a compressor or a turbine blade utilized in a turbine engine. Accordingly, and in the exemplary embodiment, object 12 includes an airfoil 14 extending outwardly from a platform 16. While the following description is directed to inspecting gas turbine engine blades, one skilled in the art will appreciate that inspection system 10 may be utilized to improve structured light imaging for any object.

System 10 also includes a structured light source 22, such as, but not limited to, a laser, a white light lamp, a light emitting diode (LED), a liquid crystal display (LCD) projector, a liquid crystal on silicon (LCOS) projector, and a digital micromirror device (DMD) projector. System 10 also includes one or more imaging sensors 24 that receive structured light reflected from object 12. In the exemplary embodiment, imaging sensor 24 is a camera that receives and creates images using structured light reflected from object 12, although other imaging sensors 24 may be used. One or more computers 26 process images received from sensors 24, and a monitor 28 may be utilized to display information to an operator. In one embodiment, computer(s) 26 include a device 30, for example, a floppy disk drive, CD-ROM drive, DVD drive, magnetic optical disk (MOD) device, and/or any other digital device including a network connecting device such as an Ethernet device for reading instructions and/or data from a computer-readable medium 32, such as a floppy disk, a CD-ROM, a DVD, and/or another digital source such as a network or the Internet, as well as yet to be developed digital means. In another embodiment, computer(s) 26 execute instructions stored in firmware (not shown). Computer(s) 26 are programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Figure 2:
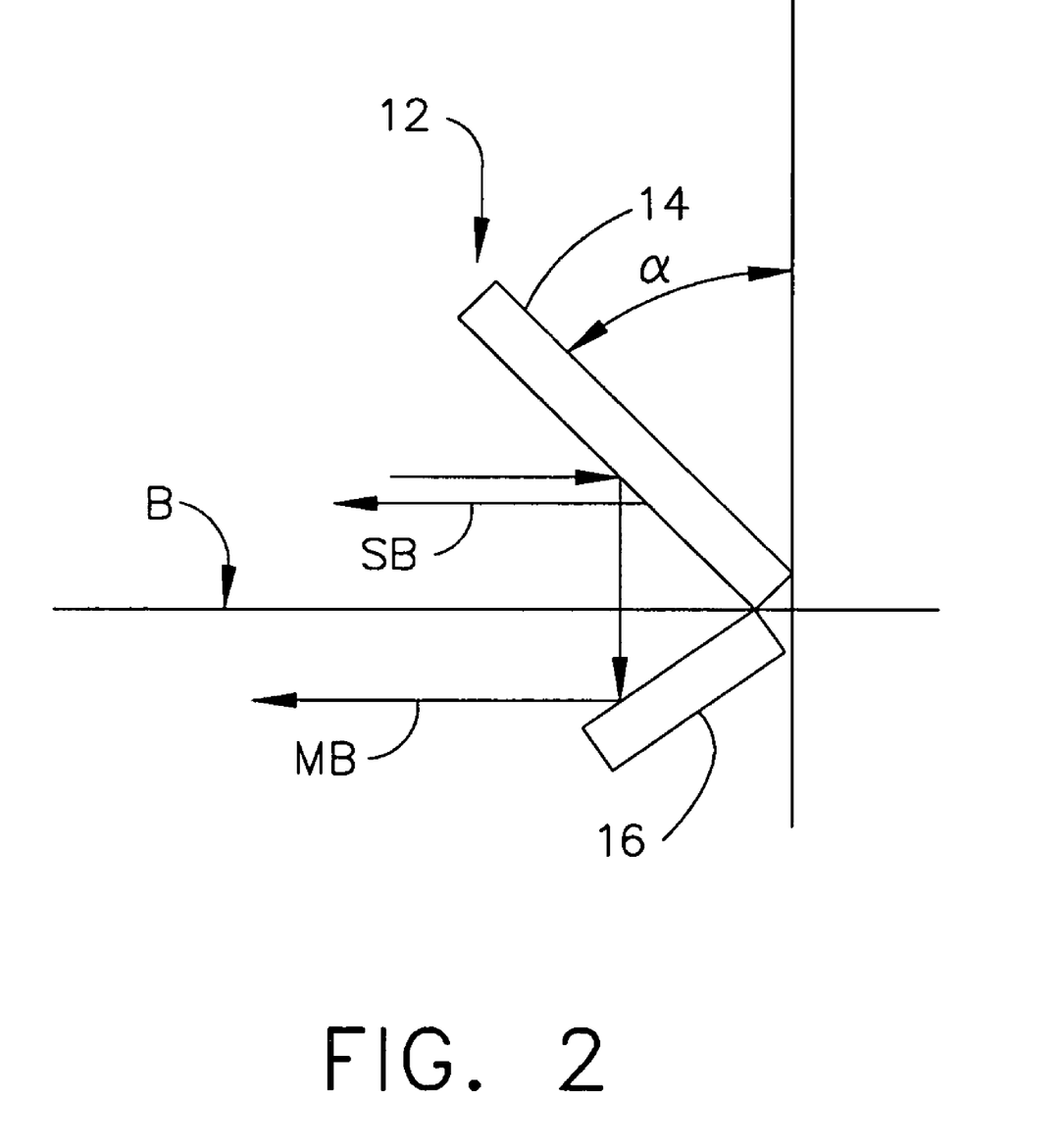
FIG. 2 is a side sectional view of an object under inspection, illustrating single and multiple bounce light paths.

FIG. 2 is a side sectional view of object 12. During operation, an object to be inspected, for example object 12, is coupled to a test fixture (not shown) and positioned proximate to system 10. In some embodiments, object 12 is orientated relative to light source 22 (shown in FIG. 1) with an angle a of orientation that enables a view to be presented to imaging sensors 24 (shown in FIG. 1) such that a plane β defined by light source 22 and imaging sensors 24 substantially bisects one or more prismatic features of object 12. For example, in the exemplary embodiment, airfoil 14 and platform 16 each define a prismatic feature of object 12.

Light source 22 is then activated causing emitted light to illuminate object 12. Imaging sensors 24 obtain an image of the emitted light pattern projected onto object 12. However, a resultant image of object 12 may include noise caused by multiple bounce reflections of the emitted light. Such noise may result in a reduced image quality and poor measurement results, possibly leading to an incorrect interpretation of surface features of object 12. For example, light reflected off of prismatic surfaces (e.g., intersecting surfaces of airfoil 14 and platform 16) of object 12 may cause multiple bounce reflections, as illustrated in FIG. 2. Directly reflected light paths, sometimes referred to as single bounce reflections, are indicated as SB in FIG. 2, and multiple bounce reflections are indicated as MB in FIG. 2. Moreover, and for example, multiple bounce reflections MB may be caused by interreflections between object 12 and portions of the test fixture illuminated by light source 22. For example, multiple bounce reflections MB may be created if the test fixture has a shape or finish that casts reflections on object 12, and/or if object 12 has a relatively mirror-like finish that reflects an image of the test fixture.

Figure 3:
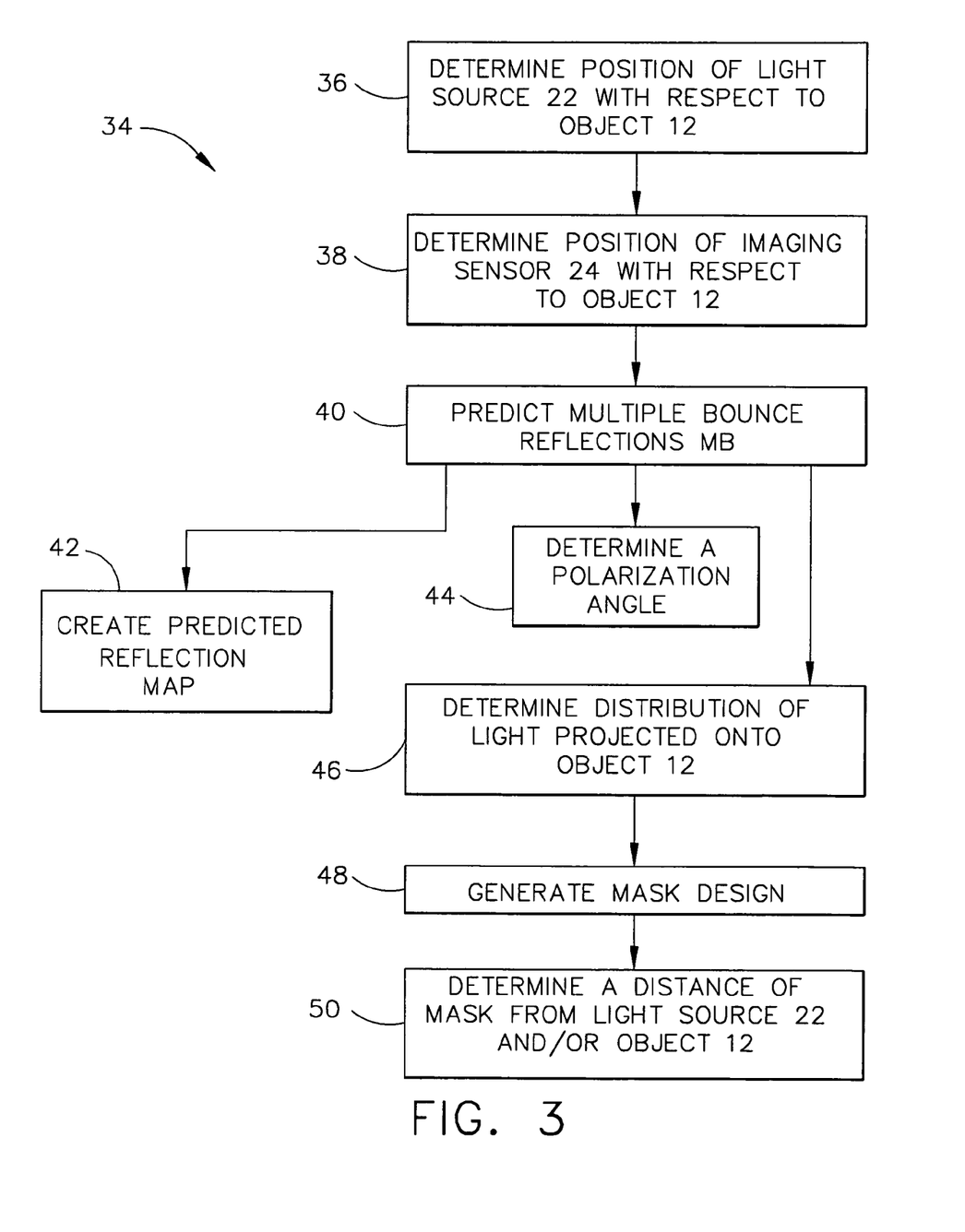
FIG. 3 is a flow chart illustrating an exemplary method for inspecting an object using the structured light measurement system shown in FIG. 1.

FIG. 3 is a flow chart illustrating an exemplary embodiment of a method 34 for inspecting object 12 (shown in FIGS. 1 and 2) using structured light measurement system 10 (shown in FIG. 1). Method 34 includes determining 36 a position of light source 22 with respect to object 12 using, for example, computer(s) 26. For example, in some embodiments determining 36 a position of light source 22 includes, but is not limited to, determining a distance of light source 22 from object 12 and/or determining an orientation, such as, but not limited to, an angle of view, of light source 22 with respect to object 12. Computer(s) 26 determine 36 a position of light source 22 with respect to object 12 to facilitate improving a quality of data obtained from inspection of object 12 using system 10. The determined position of light source 22 may facilitate producing an illumination pattern of light projected onto object 12 from light source 22 that is desired to inspect all or a particular portion of object 12. In other words, the determined position of light source 22 may facilitate producing an illumination pattern of light that is optimal for, or at least improves a quality of data obtained from, inspecting all or a particular portion of object 12. For example, in some embodiments the determined position of light source 22 facilitates producing an illumination pattern that is optimal for, or at least improves a quality of data from, inspecting object 12 to determine features thereof, such as, but not limited to surface texture, surface orientation, and/or a material used in fabricating object 12. Moreover, arid for example, in some embodiments the determined position of light source 22 facilitates producing an illumination pattern that is optimal for, or at least improves a quality of data from, inspecting particular shapes, sizes, and/or materials of object 12. Furthermore, and for example, in some embodiments the determined position of light source 22 facilitates producing an illumination pattern that facilitates reducing or eliminating uneven reflections from object 12 and/or noise caused by, for example, ambient light and/or multiple bounce reflections MB.

Computer(s) 26 determine 36 a position of light source 22 with respect to object 12 based on a three-dimensional model of object 12 and/or a three-dimensional model of system 10. Computer(s) 26 may determine a position of light source 22 using any information from the three-dimensional models of object 12 and/or system 10, such as, but not limited to, a type of light source 22, potential patterns of light emitted by light source 22, potential orientations of light source 22 with respect to object 12 and/or imaging sensor 24, a type of imaging sensor 24, potential orientations of imaging sensor 24 with respect to object 12, a size of all or a portion of object 12 to be inspected, a shape of all or a portion of object 12 to be inspected, a material of all or a portion of object 12 to be inspected, and/or a size, shape, position, and/or material of structures adjacent object 12, such as, but not limited to, a wall, a floor, a ceiling, and/or a test fixture object 12 is coupled to.

Method 34 also includes determining 38 a position of imaging sensor 24 with respect to object 12 using, for example, computer(s) 26. For example, in some embodiments determining 38 a position of imaging sensor 24 includes, but is not limited to, determining a distance of imaging sensor 24 from object 12 and/or determining an orientation, such as, but not limited to, an angle of view, of imaging sensor 24 with respect to object 12. Computer(s) 26 determine 38 a position of imaging sensor 24 with respect to object 12 to facilitate improving a quality of data obtained from inspection of object 12 using system 10. The determined position of imaging sensor 24 may facilitate receiving light reflected from object 12 in a pattern that is desired to inspect all or a particular portion of object 12. In other words, the determined position of imaging sensor 24 may facilitate receiving light reflected from object 12 in a pattern that is optimal for, or at least improves a quality of data obtained from, inspecting all or a particular portion of object 12. For example, in some embodiments the determined position of imaging sensor 24 facilitates receiving light reflected from object 12 in a pattern that is optimal for, or at least improves a quality of data from, inspecting object 12 to determine features thereof, such as, but not limited to surface texture, surface orientation, and/or a material used in fabricating object 12. Moreover, and for example, in some embodiments the determined position of imaging sensor 24 facilitates receiving light reflected from object 12 in a pattern that is optimal for, or at least improves a quality of data from, inspecting particular shapes, sizes, and/or materials of object 12. Furthermore, and for example, in some embodiments the determined position of imaging sensor 24 facilitates reducing or eliminating uneven reflections received by imaging sensor 24 from object 12 and/or noise, caused by, for example, ambient light and/or multiple bounce reflections MB, received by imaging sensor 24 from object 12.

Computer(s) 26 determine 38 a position of imaging sensor 24 with respect to object 12 based on a three-dimensional model of object 12 and/or a three-dimensional model of system 10. Computer(s) 26 may determine a position of imaging sensor 24 using any information from the three-dimensional models of object 12 and/or system 10, such as, but not limited to, a type of light source 22, potential orientations of light source 22 with respect to object 12 and/or imaging sensor 24, a type of imaging sensor 24, potential orientations of imaging sensor 24 with respect to object 12, a size of all or a portion of object 12 to be inspected, a shape of all or a portion of object 12 to be inspected, a material of all or a portion of object 12 to be inspected, and/or a size, shape, position, and/or material of structures adjacent object 12, such as, but not limited to, a wall, a floor, a ceiling, and/or a test fixture object 12 is coupled to.

Method 34 also includes predicting 40 multiple-bounce reflections MB using, for example, computer(s) 26. For example, in some embodiments computer(s) 26 create 42 a predicted reflection map of the illuminated surface of object 12. Computer(s) 26 predict 40 multiple bounce reflections to facilitate improving a quality of data obtained from inspection of object 12 using system 10, for example by reducing or eliminating image noise. In some embodiments, method 34 may include determining 44 a polarization angle that facilitates reducing the predicted multiple bounce reflections MB. Once a polarization angle has been determined 44, suitable means, such as, but not limited to, polarization filters may be used to facilitate reducing or eliminating multiple bounce reflections MB.

Computer(s) 26 predict 40 multiple bounce reflections MB based on the three-dimensional model of object 12, the three-dimensional model of system 10, and/or the determined position of light source 22 and/or imagining sensor 24. Computer(s) 26 may predict 40 multiple bounce reflections MB using any information from the determined positions of light source 22 and/or imaging sensor 24, and/or from the three-dimensional models of object 12 and/or system 10. Such information from the three-dimensional models of object 12 and/or system 10 may include, but is not limited to, a type of light source 22, potential patterns of light emitted by light source 22, potential orientations of light source 22 with respect to object 12 and/or imaging sensor 24, a type of imaging sensor 24, potential orientations of imaging sensor 24 with respect to object 12, a size of all or a portion of object 12 to be inspected, a shape of all or a portion of object 12 to be inspected, a material of all or a portion of object 12 to be inspected, and/or a size, shape, position, and/or material of structures adjacent object 12, such as, but not limited to, a wall, a floor, a ceiling, and/or a test fixture object 12 is coupled to.

Method 34 also includes determining 46 a distribution of light projected onto object 12 by light source 22 using, for example, computer(s) 26. More specifically, computer(s) 26 determine 46 a distribution of light levels over different areas the illuminated surface of object 12. Computer(s) 26 determine 46 a distribution of light projected onto object 12 to facilitate improving a quality of data obtained from inspection of object 12 using system 10. For example, the determined distribution may facilitate reducing or eliminating areas of the illuminated surface of object 12 that are too light or too dark to measure using system 10. Moreover, and for example, the determined distribution may facilitate reducing or eliminating multiple bounce reflections MB. As such, the determined distribution of light may facilitate producing a distribution of light that is optimal for, or at least improves a quality of data obtained from, inspecting all or a particular portion of object 12.

Computer(s) 26 determine 46 a distribution of light projected onto object 12 based on the three-dimensional model of object 12, the three-dimensional model of system 10, the determined position of light source 22 and/or imagining sensor 24, and/or the predicted multiple bounce reflections MB. Computer(s) 26 may determine 46 a distribution of light projected onto object 12 using any information from the determined positions of light source 22 and/or imaging sensor 24, the predicted multiple bounce reflections MB, and/or from the three-dimensional models of object 12 and/or system 10. Such information from the three-dimensional models of object 12 and/or system 10 may include, but is not limited to, a type of light source 22, potential patterns of light emitted by light source 22, potential orientations of light source 22 with respect to object 12 and/or imaging sensor 24, a type of imaging sensor 24, potential orientations of imaging sensor 24 with respect to object 12, a size of all or a portion of object 12 to be inspected, a shape of all or a portion of object 12 to be inspected, a material of all or a portion of object 12 to be inspected, and/or a size, shape, position, and/or material of structures adjacent object 12, such as, but not limited to, a wall, a floor, a ceiling, and/or a test fixture object 12 is coupled to. Once a distribution of light projected onto object 12 is determined 46, system 10 may control such distribution using any suitable means, such as, but not limited to, a film-type attenuator and/or light source 22, for example when light source 22 is an LCD projector, a LCOS projector, and/or a DMD projector.

Method 34 also includes generating 48 a mask design that facilitates blocking light emitted from light source 22 from illuminating a portion of object 12 outside a profile of object 12 to be inspected using, for example, computer(s) 26. More specifically, computer(s) 26 generate 48 a design for a mask that includes an opening for channeling light emitted from light source 22 in a pattern that substantially matches the profile of object 12 to be inspected. As such, the generated mask design may facilitate reducing or eliminating noise caused by, for example, inter-reflections between object 12 and adjacent structure, such as, but not limited to, a wall, a floor, a ceiling, and/or a test fixture object 12 is coupled to. Accordingly, computer(s) 26 generate 48 a mask design that facilitates improving a quality of data obtained from inspection of object 12 using system 10. Moreover, the generated mask design may facilitate producing an illumination pattern on object 12 that is optimal for, or at least improves a quality of data obtained from, inspecting all or a particular portion of object 12 (e.g., the profile of object 12 to be inspected).

To generated the mask design, computer(s) 26 may determine 50 a distance of the mask from object 12 and/or from light source 22 that, combined with a size and shape of the mask opening, facilitates providing an illumination pattern that substantially matches the profile of object 12 to be inspected. In some embodiments, computer(s) 26 generate 48 the mask design based on the three-dimensional model of object 12, measurements of object 12, the three-dimensional model of system 10, and/or the determined position of light source 22 and/or imagining sensor 24. Computer(s) 26 may generate 48 the mask design using any information from the determined positions of light source 22 and/or imaging sensor 24, and/or from the three-dimensional models of object 12 and/or system 10. Such information from the three-dimensional models of object 12 and/or system 10 may include, but is not limited to, a type of light source 22, potential patterns of light emitted by light source 22, potential orientations of light source 22 with respect to object 12 and/or imaging sensor 24, a type of imaging sensor 24, potential orientations of imaging sensor 24 with respect to object 12, a size of all or a portion of object 12 to be inspected, a shape of all or a portion of object 12 to be inspected, a material of all or a portion of object 12 to be inspected, and/or a size, shape, position, and/or material of structures adjacent object 12, such as, but not limited to, a wall, a floor, a ceiling, and/or a test fixture object 12 is coupled to. Alternatively, the mask is generated manually by an operator.

Once a mask design has been generated 48, the mask may be fabricated using any suitable methods and/or means, such as, but not limited to, manually fabricating the mask using hand tools and/or automatically fabricating the mask using a machine, such as, but not limited to, a computer numerical control (CNC) machine.

Figure 4:
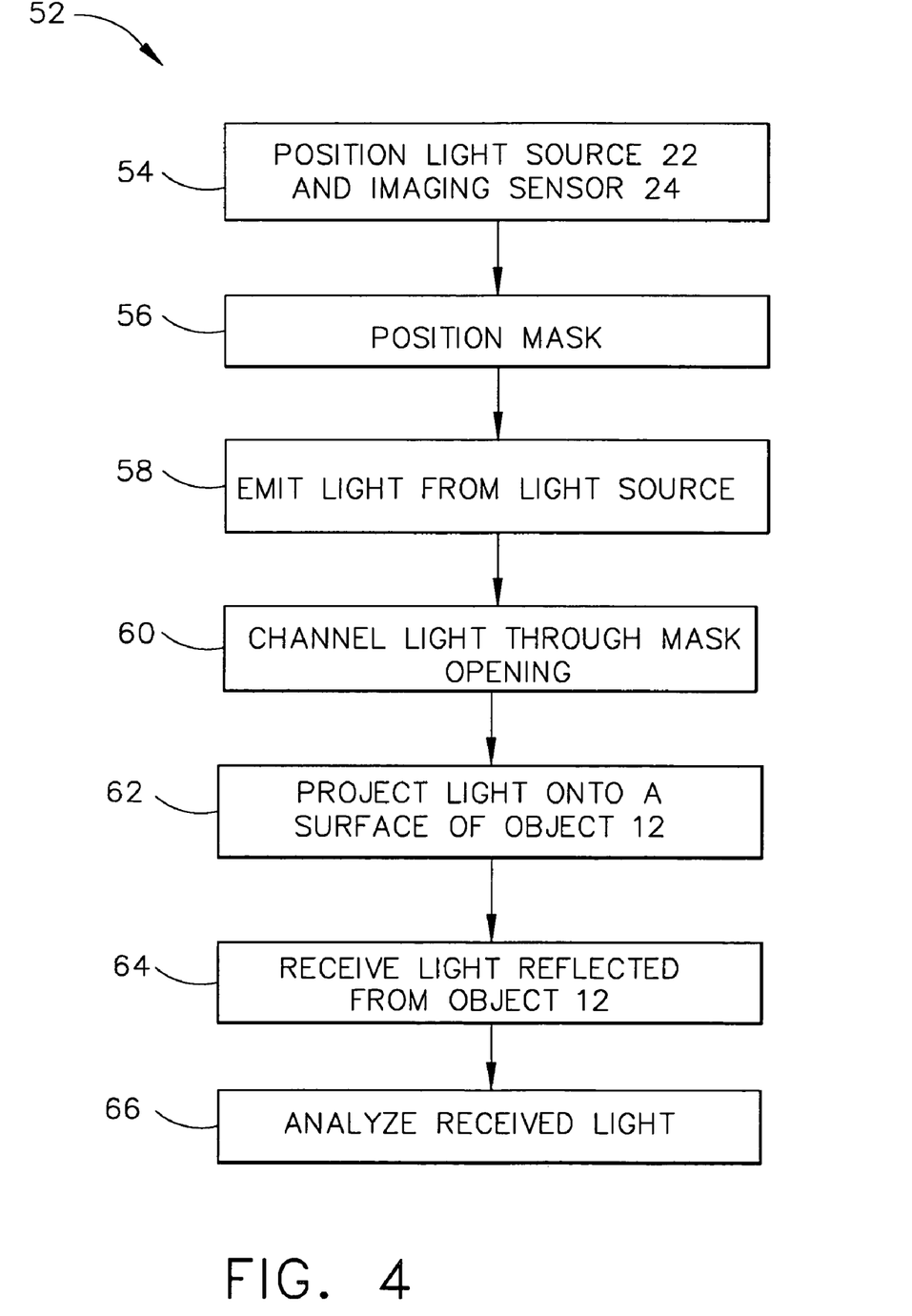
FIG. 4 is a flow chart illustrating another exemplary method for inspecting an object using the structured light measurement system shown in FIG. 1.

FIG. 4 is a flow chart illustrating an exemplary embodiment of a method 52 for inspecting object 12 (shown in FIGS. 1 and 2) using structured light measurement system 10 (shown in FIG. 1). Method 52 includes positioning 54 light source 22 and imaging sensor 24 with respect to object 12 based on the determined position of light source 22 and the determined position of imaging sensor 24. Method 52 may also include positioning 56 a mask at a determined distance from object 12 and/or light source 22. Light is then emitted 58 from light source 22 such that light is channeled 60 through the mask opening projected 62 onto a surface of object 12. Light projected onto object 12 is reflected therefrom and received 64 by imaging sensor 24. The received light is then analyzed 66, using, for example, conventional image processing techniques, to facilitate inspecting at least a portion of object 12, such as, but not limited to, identifying multiple bounce reflections MB and/or features of object 12, such as, but not limited to, surface texture, surface orientation, and a material used in fabricating object 12.

The methods and systems described and/or illustrated herein facilitate automatically determining desired positions of a light source and an imaging sensor with respect to object 12 to facilitate improving a quality of data obtained from inspection of object 12 using system 10. The determined position of light source 22 may facilitate producing an illumination pattern of light projected onto object 12 from light source 22 that is optimal for, or at least improves a quality of data obtained from, inspecting all or a particular portion of object 12. The determined position of imaging sensor 24 may facilitate receiving light reflected from object 12 in a pattern that is optimal for, or at least improves a quality of data obtained from, inspecting all or a particular portion of object 12. Moreover, the methods and systems described and/or illustrated herein facilitate predicting multiple-bounce reflections MB to facilitate improving a quality of data obtained from inspection of object 12 using system 10, for example by reducing or eliminating image noise. The methods and systems described and/or illustrated herein may also facilitate determining a polarization angle that facilitates reducing the predicted multiple bounce reflections MB. Furthermore, the methods and systems described and/or illustrated herein may facilitate determining a distribution of light projected onto object 12 by light source 22 to facilitate improving a quality of data obtained from inspection of object 12 by, for example, reducing or eliminating areas of the illuminated surface of object 12 that are too light or too dark to measure using system 10. Moreover, and for example, the determined distribution may facilitate reducing or eliminating multiple bounce reflections MB. Additionally, the methods and systems described and/or illustrated herein may facilitate generating a mask design that facilitates blocking light emitted from light source 22 from illuminating a portion of object 12 outside a profile of object 12 to be inspected. As such, the generated mask design may facilitate reducing or eliminating noise caused by, for example, interreflections between object 12 and adjacent structure, such as, but not limited to, a wall, a floor, a ceiling, and/or a test fixture object 12 is coupled to. As technical effect of the methods and systems described and/or illustrated herein includes facilitating improving a quality of data obtained from inspection of object 12 by automatically determining desired positions of a light source and an imaging sensor with respect to object 12, predicting multiple-bounce reflections MB, determining a polarization angle that facilitates reducing the predicted multiple bounce reflections MB, determining a distribution of light projected onto object 12 by light source 22, and/or generating a mask design that facilitates blocking light emitted from light source 22 from illuminating a portion of object 12 outside a profile of object 12 to be inspected.

Although the systems and methods described and/or illustrated herein are described and/or illustrated with respect to gas turbine engine components, and more specifically an engine blade for a gas turbine engine, practice of the systems and methods described and/or illustrated herein is not limited to gas turbine engine blades, nor gas turbine engine components generally. Rather, the systems and methods described and/or illustrated herein are applicable to any object.

Exemplary embodiments of systems and methods are described and/or illustrated herein in detail. The systems and methods are not limited to the specific embodiments described herein, but rather, components of each system, as well as steps of each method, may be utilized independently and separately from other components and steps described herein. Each component, and each method step, can also be used in combination with other components and/or method steps.

When introducing elements/components/etc. of the assemblies and methods described and/or illustrated herein, the articles "a", "an", "the" and "said" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc.

While the invention has been described in terms of various specific embodiments, those skilled in the art will recognize that the invention can be practiced with modification within the spirit and scope of the claims.

What is claimed is:

1. A method for inspecting an object using a structured light measurement system that includes a light source for projecting light onto a surface of the object and an imaging sensor for receiving light reflected from the object, said method comprising:
   determining a position of at least one of the light source and the imaging sensor with respect to the object based on at least one of a three-dimensional model of the object and a three-dimensional model of the structured light measurement system;
   predicting multiple-bounce reflections of the projected light reflected from the object; and
   displaying the determined position of at least one of the light source and the imaging sensor.

2. A method in accordance with claim 1 wherein predicting multiple-bounce reflections of the projected light reflected from the object comprises predicting multiple-bounce reflections based on at least one of the three-dimensional model of the object, the three-dimensional model of the structured light measurement system, and the determined position of at least one of the light source and the imaging sensor.

3. A method in accordance with claim 2 further comprising determining a distribution of light projected onto the object based on at least one of the three-dimensional model of the object, the three-dimensional model of the structured light measurement system, the determined position of at least one of the light source and the imaging sensor, and the predicted multiple-bounce reflections.

4. A method in accordance with claim 2 further comprising determining a polarization angle that facilitates reducing the predicted multiple bounce reflections.

5. A method in accordance with claim 1 further comprising generating a mask that facilitates blocking light from illuminating a portion of the object outside a profile of the object to be inspected based on at least one of the three-dimensional model of the object, the three-dimensional model of the structured light measurement system, and a determined position of the light source.

6. A method in accordance with claim 5 further comprising determining a distance of the mask from at least one of the object and the light source based on at least one of the three-dimensional model of the object, the three-dimensional model of the structured light measurement system, and the determined position of the light source.

7. A method in accordance with claim 1 wherein determining a position of at least one of the light source and the imaging sensor with respect to the object comprises determining at least one of an orientation and a distance of at least one of the light source and the imaging sensor with respect to the object.

8. A method for inspecting an object using a structured light measurement system that includes a light source for projecting light onto a surface of the object and an imaging sensor for receiving light reflected from the object, said method comprising:
   determining a position of at least one of the light source and the imaging sensor with respect to the object based on at least one of a three-dimensional model of the object and a three-dimensional model of the structured light measurement system;
   predicting multiple-bounce reflections of the projected light reflected from the object;
   positioning at least one of the light source and the imaging sensor with respect to the object based on the determined position;
   emitting light from the light source;
   projecting light emitted from the light source onto a surface of the object;
   receiving light reflected from the object surface with the imaging sensor; and
   analyzing the light received by the imaging sensor to facilitate inspecting at least a portion of the object.

9. A method in accordance with claim 8 wherein predicting multiple-bounce reflections of the projected light reflected from the object comprises predicting multiple-bounce reflections based on at least one of the three-dimensional model of the object, the three-dimensional model of the structured light measurement system, and the determined position of at least one of the light source and the imaging sensor.

10. A method in accordance with claim 9 wherein predicting multiple bounce reflections comprises creating a predicted reflection map of a portion of the object illuminated by the light source.

11. A method in accordance with claim 9 further comprising determining a distribution of light projected onto the object based on at least one of the three-dimensional model of the object, the three-dimensional model of the structured light measurement system, the determined position of at least one of the light source and the imaging sensor, and the predicted multiple bounce reflections.

12. A method in accordance with claim 9 further comprising determining a polarization angle that facilitates reducing the predicted multiple bounce reflections.

13. A method in accordance with claim 8 further comprising:
   generating a mask based on at least one of the three-dimensional model of the object, the three-dimensional model of the structured light measurement system, and a determined position of the light source; and
   channeling light emitted from the light source through the mask to facilitate blocking light from illuminating a portion of the object outside a profile of the object to be inspected.

14. A method in accordance with claim 13 further comprising:
   determining a distance of the mask from at least one of the object and the light source based on at least one of the three-dimensional model of the object, the three-dimensional model of the structured light measurement system, and the determined position of the light source; and
   positioning the mask at the determined distance.

15. A method in accordance with claim 8 wherein determining a position of at least one of the light source and the imaging sensor with respect to the object comprises determining at least one of an orientation and a distance of at least one of the light source and the imaging sensor with respect to the object.

16. A method in accordance 8 wherein analyzing light received by the image sensor comprises identifying at least one of a surface texture, a surface orientation, and a material used in fabricating the object based on light received by the imaging sensor.

17. A structured light measurement system for inspecting an object, said structured light measurement system comprising:
   a structured light source configured to project structured light onto a surface of the object;
   an imaging sensor configured to receive structured light reflected from the object surface; and a computer configured to:
  determine a position of at least one of said structured light source and said imaging sensor with respect to the object based on at least one of a three-dimensional model of the object and a three-dimensional model of said structured light measurement system; and
  predict multiple-bounce reflections of said structured light reflected from the object.

18. A system in accordance with claim 17 wherein said computer is further configured to:
  predict multiple-bounce reflections of said structured light reflected from the object based on at least one of the three-dimensional model of the object, the three-dimensional model of said structured light measurement system, and the determined position of at least one of said structured light source and said imaging sensor; and
  determine a polarization angle that facilitates reducing the predicted multiple bounce reflections.

19. A system in accordance with claim 18 wherein said computer is further configured to determine a distribution of light projected onto the object based on at least one of the three-dimensional model of the object, the three-dimensional model of said structured light measurement system, the determined position of at least one of said structured light source and said imaging sensor, and the predicted multiple bounce reflections.

20. A system in accordance with claim 17 wherein said computer is further configured to generate a mask that facilitates blocking light from illuminating a portion of the object outside a profile of the object to be inspected based on at least one of the three-dimensional model of the object, the three-dimensional model of the structured light measurement system, and the determined position of at least one of said structured light source and said imaging sensor.

* * * * *